United States Patent
Baxter et al.

(10) Patent No.: US 6,712,286 B2
(45) Date of Patent: Mar. 30, 2004

(54) SYSTEM, APPARATUS, AND METHODS FOR DISPENSING SCENT BLOCKER AND ANIMAL LURE AND MARKING TRAIL DURING HUNTING AND OTHER OUTDOOR EXCURSIONS

(76) Inventors: Doug Baxter, 985 Storybook La., Oviedo, FL (US) 32765; Frank Sloan, 510 Kelly Green St., Oviedo, FL (US) 32765

( * ) Notice: Subject to any disclaimer, the term of this patent is extended or adjusted under 35 U.S.C. 154(b) by 267 days.

(21) Appl. No.: 09/933,370

(22) Filed: Aug. 20, 2001

(65) Prior Publication Data

US 2003/0034403 A1 Feb. 20, 2003

(51) Int. Cl.[7] .............................. A24F 25/00; A61L 9/04
(52) U.S. Cl. .............................. 239/36; 239/43; 239/46; 239/47
(58) Field of Search .............................. 239/36, 43, 44, 239/46, 47, 51, 51.5, 53, 54, 55, 56, 57, 60; 222/175

(56) References Cited

U.S. PATENT DOCUMENTS

| | | |
|---|---|---|
| 1,780,407 A | 11/1930 | Smith |
| 2,235,350 A | 3/1941 | Anderson |
| 4,722,477 A | 2/1988 | Floyd .......................... 239/36 |
| 4,735,010 A | 4/1988 | Grinarml ........................ 43/1 |
| 5,074,439 A | 12/1991 | Wilcox ........................ 222/175 |
| 5,327,667 A | 7/1994 | Fore ................................ 43/1 |
| 5,738,398 A | 4/1998 | Miano ........................ 294/1.1 |
| 5,756,180 A | * 5/1998 | Squires et al. ................. 428/90 |
| 5,857,217 A | 1/1999 | Hsuch ............................ 2/170 |
| 5,863,633 A | * 1/1999 | Squires et al. ................. 428/90 |
| 5,906,298 A | 5/1999 | Ward ........................ 222/175 |
| D430,350 S | 8/2000 | Stachowski .................. D28/39 |
| 6,116,251 A | 9/2000 | Stachowski ................. 132/273 |

* cited by examiner

*Primary Examiner*—Davis Hwu
(74) *Attorney, Agent, or Firm*—Allen, Dyer, Doppelt, Milbrath & Gilchrist, P.A.

(57) ABSTRACT

A system for dispersing a scent and marking a trail useful in hunting and other outdoor endeavors is provided, the system providing for easily positioning a self-fastening scent dispenser and marker to a preselected structure as well as the person and apparel of a user. The apparatus includes a camouflage cover so that the apparatus can easily be concealed when in use. A reflector can also be included, however, so that the apparatus can be located in the dark using a generated light beam, while also protecting the user by identifying the user to other hunters in the area. Methods are also provided to permit a hunter or hiker to readily attach the self-fastening scent dispenser and trail marker as the user moves along a trail during a hunt, hike, or other outdoor excursion.

52 Claims, 6 Drawing Sheets

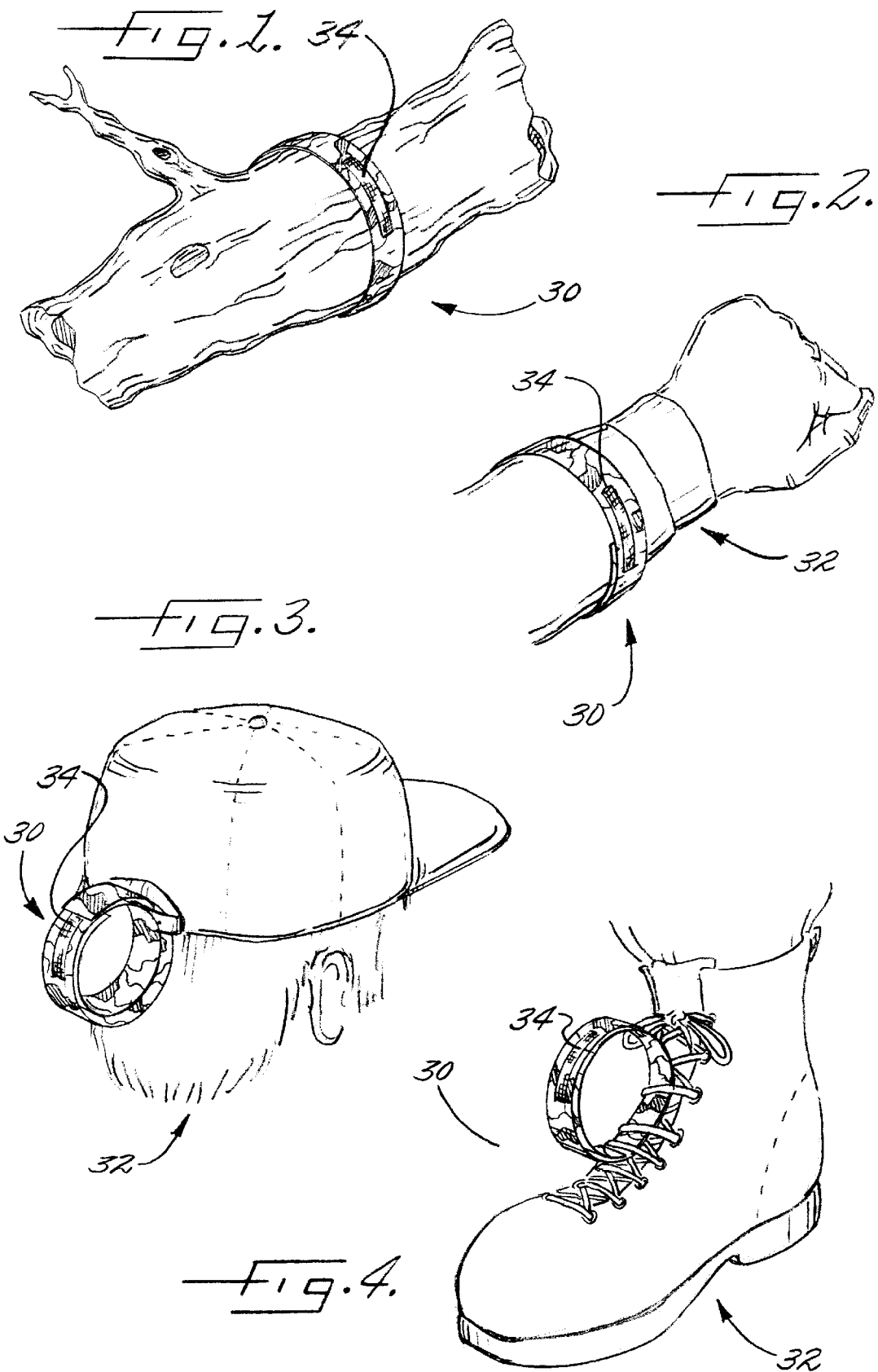

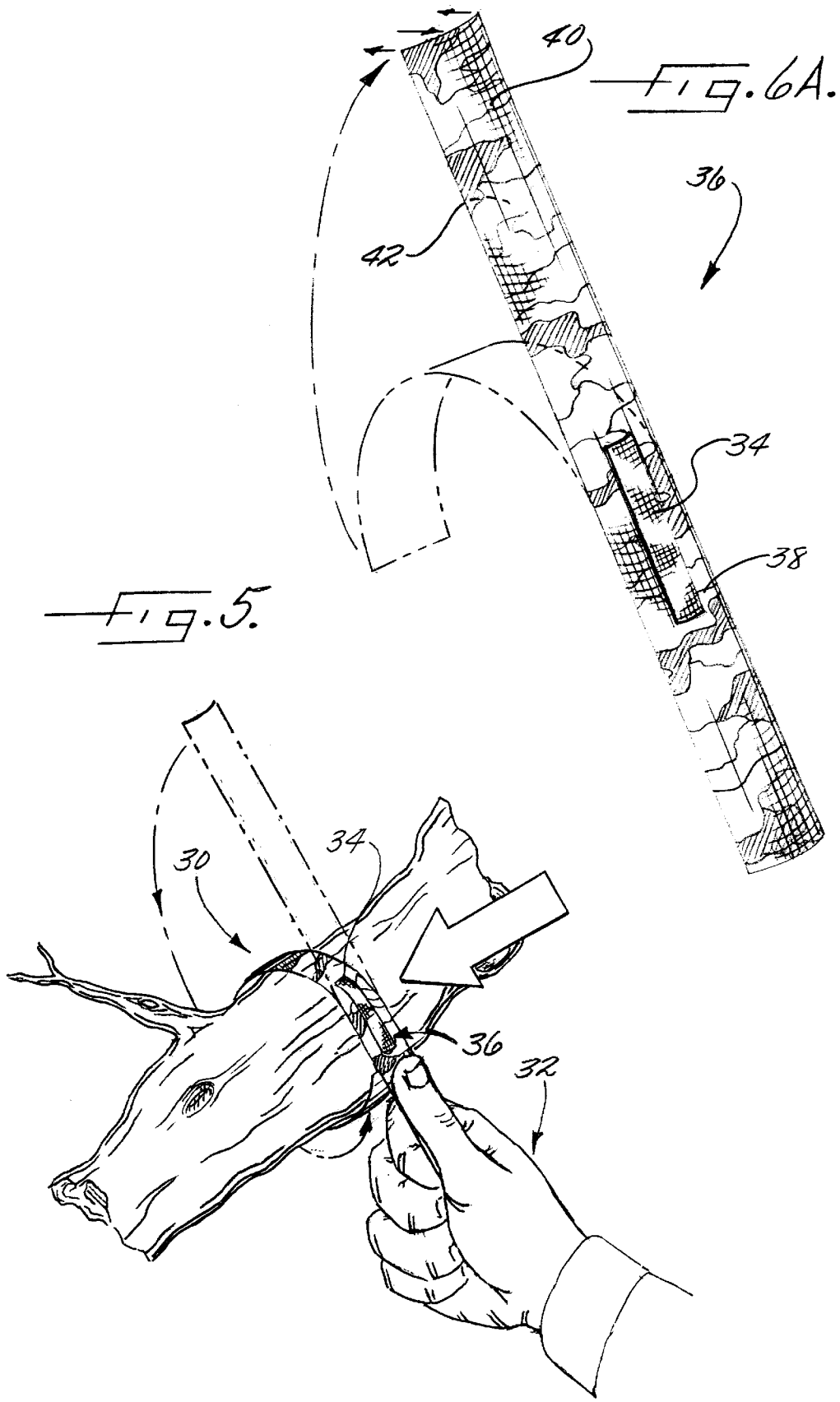

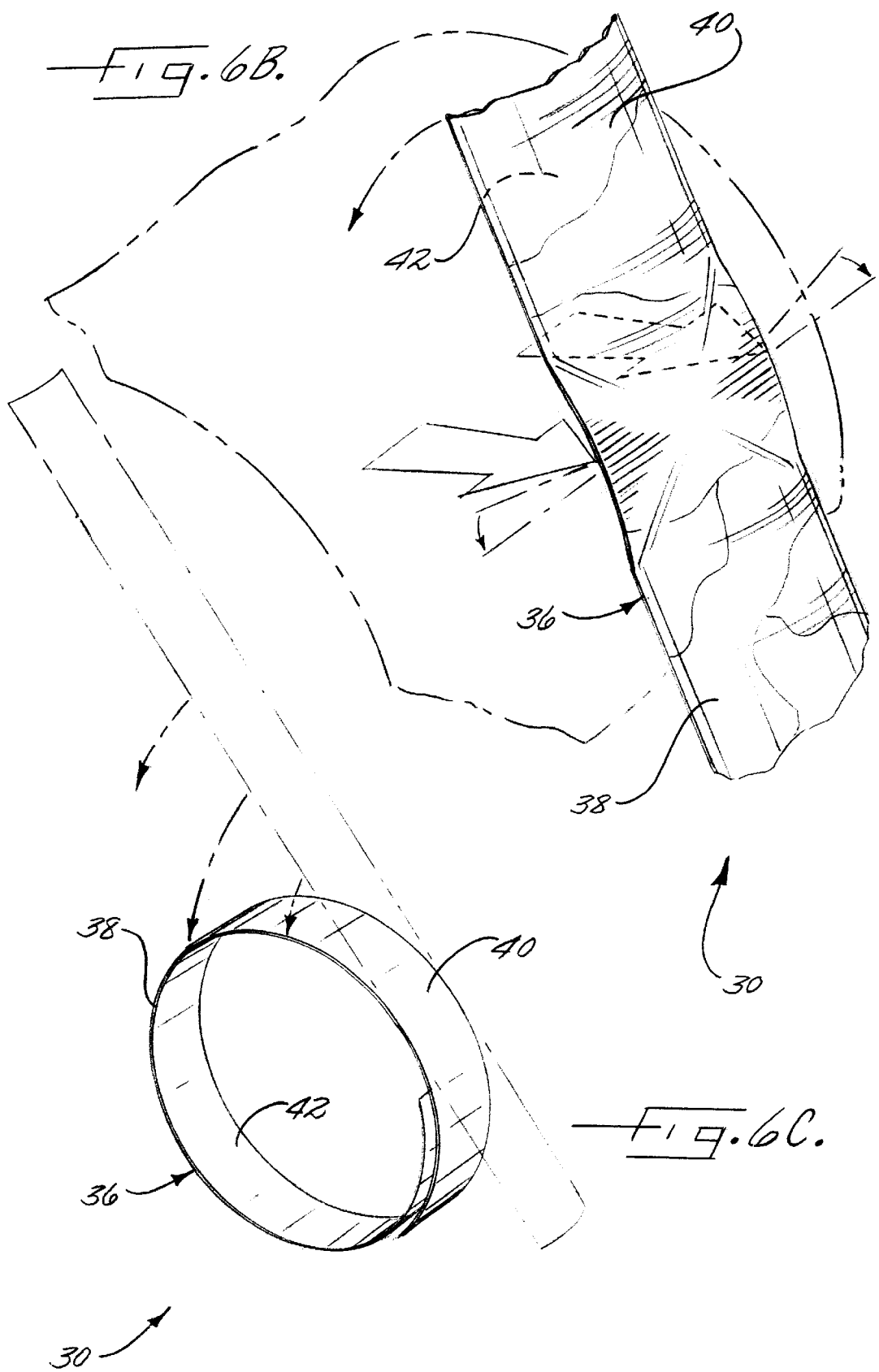

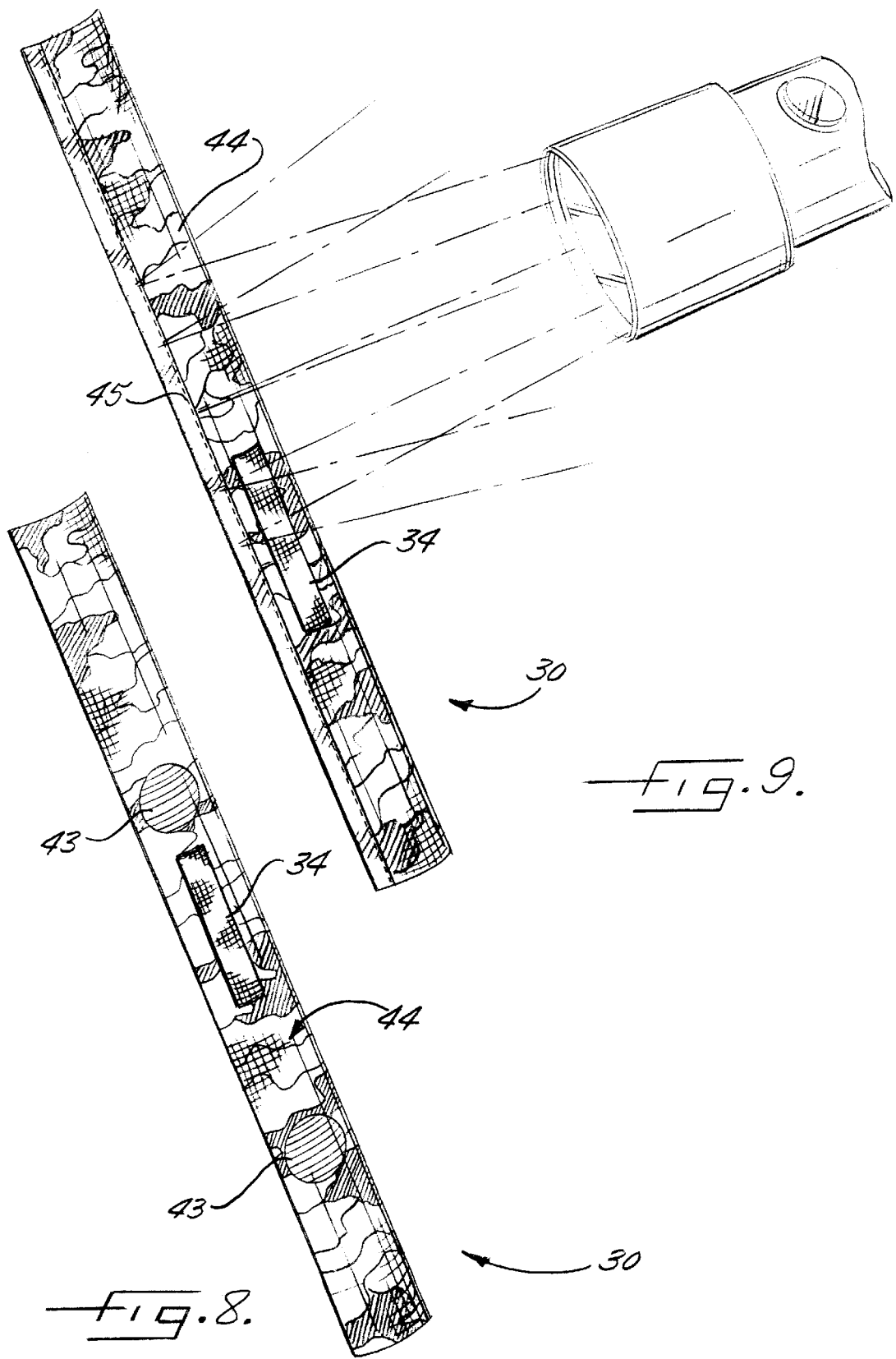

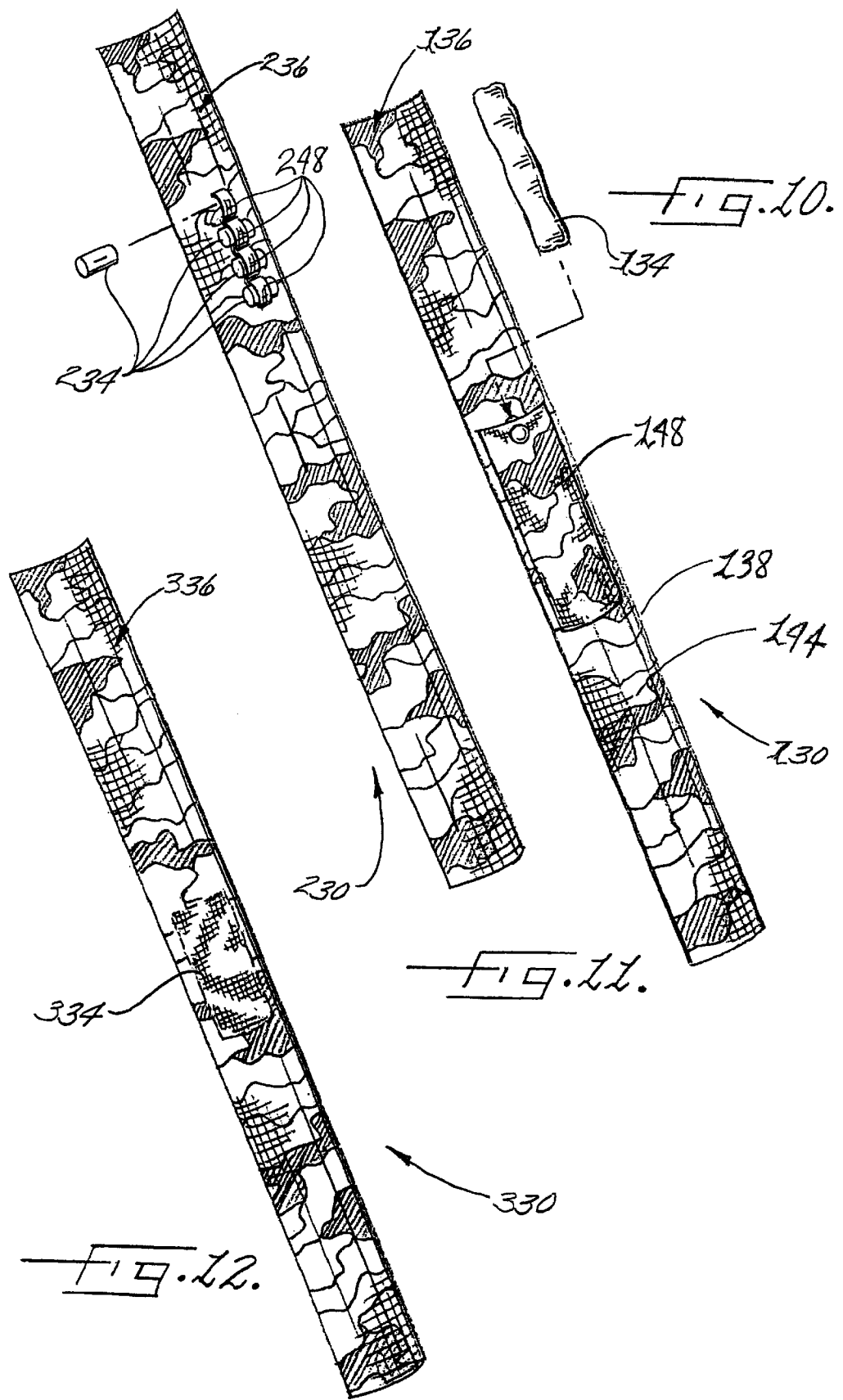

SYSTEM, APPARATUS, AND METHODS FOR DISPENSING SCENT BLOCKER AND ANIMAL LURE AND MARKING TRAIL DURING HUNTING AND OTHER OUTDOOR EXCURSIONS

FIELD OF THE INVENTION

The present invention relates to the field of outdoor activities and, more particularly, to the fields of dispensing a scent during a hunting excursion and marking a trail during a recreational or work-related outdoor venture.

BACKGROUND OF THE INVENTION

Hunters of deer and other game animals frequently rely on some type of animal lure to assist them in tracking and sighting game. Usually, the lure a hunter employs is a scented substance, the odor of which is an animal attractant. Other scented substances likewise are used to mask natural odors associated with the hunter that would otherwise warn the animal of the hunter's presence thereby hindering the hunter's ability to track the animal.

Many of the commercially available scented substances are provided in liquid form and applied directly to the clothes or boots of the hunter. The scent, however, ordinarily wears off relatively quickly because of the type of fabrics commonly used for hunting apparel. This tendency is exacerbated by rain and other weather conditions the hunter frequently encounters during an outdoor excursion, as well as by the hunter's brushing against tree limbs and shrubs as the hunter moves through a wooded area in pursuit of prey.

Various types of devices have attempted to deal with some of these problems. For example, U.S. Pat. No. 4,735,010 to Grinarmi titled Scent Dispenser For Attachment Under A Shoe suggest positioning a tubular dispenser within the arch on the underside of a hunter's boot, the tube being held in place by a tie extending the laces of the boot. The problem, however, is that, so positioned, the device is all the more exposed to mud and rain puddles rendering the device less effective and reducing its effective life. The device can also be tedious to apply, requiring the hunter to reach down, loop the device around the hunter's boot and, fasten the device with a buckle or other fastener.

U.S. Pat. No. 4,722,477 to Floyd titled Scented Hunting Strap, is somewhat similar to the Grinarmi device in relying on a strap having a pair of fasteners such as buckles or complementary hook-and-loop portions that permit the strap to be secured to the hunter's angle or arm, or a separate object. Floyd, however, also requires that the hunter stop and apply the device by using both hands so as to wrap the device and then connect the fasteners. To replace the scent while hunting, the hunter must stop and use both hands to secure the device. This not only interrupts the hunter's stalking, but also can create noises as the hunter works to secure the device with a buckle or other such fastener—noises that can alert the hunter's prey to the hunter's presence.

As an alternative, U.S. Pat. No. 5,074,439 to Wilcox titled Scent Lure Dispensing Device suggests attaching a container to the hunter's ankle to be dragged along behind as the hunter moves along a trail. This device, however, is clumsy in that it drags behind the hunter and also can be noisy, thereby alerting the prey to the hunter's presence and accordingly undercutting the very purpose of the device. U.S. Pat. No. 5,327,667 to Fore titled Device For Luring Deer avoids positioning the device on the sole of the hunter's boot or dragging it behind the hunter by providing an adhesive strip that attaches, for example, to the toe of the boot. This, nonetheless poses many of the limitations as with Grinarmi, namely that the device is still largely exposed to mud and rain puddles thereby reducing its effectiveness and longevity. Perhaps more importantly, as with each of the other devices, the hunter must stop any other activity and use two hands to attach the device to a boot and secure it there.

There thus is a need for a device for dispensing a scent quickly and efficiently without having to stop, position the device, and fasten it in place with a buckle or other fastener requiring use of both hands.

SUMMARY OF THE INVENTION

With the foregoing in mind, the present invention advantageously provides an apparatus that more easily and more readily attaches a scent dispenser to a pre-selected object. More specifically, the apparatus according to the present invention permits a hunter to rapidly, in one movement, single handedly attach a scent dispenser to a tree limb, a rung on a ladder, or any other conveniently positioned object. In this way, the hunter is able to move along a trail laying down a scent intended to attract a deer or other animal without even stopping. The hunter is able to move quietly and quickly along a chosen path while efficiently deploying scent dispensers at strategically chosen locations. The hunter thus can easily lay out the scent along a trail leading directly to the hunter's stand.

At the same time, the apparatus also can be used to dispense a scent blocker so as to mask the hunter's scent. The scent dispenser easily attaches to the hunter's arm, wrist, or ankle. Just as easily it can be attached to a lace of the hunter's boot or the band of the hunter's cap. The scent dispenser thus provides a convenient and effective dispersal of the scent blocker so as to mask animal-alarming scents associated with the hunter as well as the hunter's apparel and equipment. Blocking these scent's permits the hunter to move more efficaciously along the trail and to position him or herself at a strategically located hunter's stand.

According to the present invention, the apparatus provides additional advantages as well as scent dispensing and scent blocking. For example, the apparatus can be covered with a material having a pattern pre-selected to include the colors of the foliage of the environment for the season in which the hunter is engaged. Thus, the apparatus is effectively camouflaged. Moreover, while substantially camouflaging the apparatus, the cover material can include a limited-size marker such as a single, small bright orange spot. This can allow the hunter to easily locate in daylight the location of the apparatus. Conversely, if the apparatus is attached to the hunter's person, apparel, or equipment, the marker can serve to caution other hunters in the vicinity of the hunter's presence. So too, the marker can serve to identify for the hunter the perimeters of a chosen field of fire. Likewise, the marker can serve as a range gauge that can be viewed from a distance as the hunter is positioned at his or her stand. The apparatus can further include a signal reflector (e.g., a light reflector) so that the apparatus can be located in the dark using light generated, for example, by a flashlight.

The various features of the apparatus provide a system, moreover, for dispensing and blocking scents as well as marking trails and fields-of-fire perimeters and ranges. The apparatus, specifically, can be used jointly with multiple, identical devices to provide a system whereby the hunter is able to move quietly and quickly along a trail efficiently attaching the combination scent dispenser-marker to preselected objects as described above. The hunter, then, can return finding his or her way along the same path guided by the plurality of combination scent dispenser-markers. The visible mark in day and the light reflector at night permit the hunter not only to find his or her way along the trail, but also easily retrieve the plurality of combination scent dispenser-markers already deployed. The retrieved scent dispenser-markers can be replenished and redeployed during a subsequent hunting excursion.

The self-fastening capability of the apparatus provides a significant advantage over conventional devices. Conventional devices rely on straps, belts, and similar attaching devices which are not only cumbersome but are also slow to effect and require the hunter to put down his or her gun or other equipment so as to be able to use both hands to position the device and connect up the buckles or other fastening members. In sharp contrast, the apparatus according to the present invention permits single-handed attachment in a single movement. Specifically, the apparatus is readily attached by striking the apparatus against the pre-selected object. The apparatus is self-fastening. Therefore, with one hand, the apparatus can be deployed and secured to an object by striking the object with the apparatus. Attachment is preferably effected with an attachment that is a generally rectangular strip biased to take on and remain in a coiled alignment unless stretched out into a substantially elongate shape.

More specifically, the apparatus preferably includes a substantially elongate body, preferably formed of a semi-rigid material. The substantially elongate body has a substantially convex first surface with the direction of curvature of the convex surface being substantially perpendicular to the direction of elongation and a substantially concave second surface opposite the first with the direction of curvature of the concave surface, again, being substantially perpendicular to the direction of elongation of the substantially elongate body. Thus, the apparatus can be stretched into a substantially elongate alignment with the convex and concave surfaces of the elongate body supplying resistance to the body's natural tendency to coil. When struck, however, the body's tendency to coil is not impeded and the force of the blow tends to flatten out the convex and concave surfaces so that it self-fastens to the object struck.

The self-fastening capability of the apparatus provides considerable advantages. Among these are the ability of the user to be able to single handedly attach the scent dispenser to a pre-selected object by simply tapping the pre-selected object with a modest amount of force. During a typical hunting excursion, the hunter can move through a wooded area and at selected points stop and draw from his or her jacket a scent dispenser connected to the scent dispenser attachment. Quietly, the hunter can gently strike a tree limb or branch and easily and quickly attach thereto the scent dispenser. Thus, the hunter can lay out a scent line leading directly to the hunter's stand. When the hunter reaches his or her stand, another scent dispenser can be attached using the scent dispenser attachment to a rung on the ladder leading to the stand perched off the ground.

The same apparatus can just as readily be used with a scent blocker already described, in which case the scent dispenser can be attached using the scent dispenser attachment by threading it under the laces of the hunter's boot, tapping it against the hunter's ankle or wrist, or even wrapping it over the adjustment band of the hunter's cap.

The present invention also provides a method for dispensing a scent. Specifically, the method includes providing at least one scent dispenser and at least one corresponding scent dispenser attachment adapted to receive and hold a scent dispenser. Moreover, the at least one scent dispenser attachment is capable of self-fastening to a pre-selected object whenever a user strikes the at least one scent dispenser attachment against an object. The method can include camouflaging the at least one scent dispenser and scent dispenser attachment by at least partially covering each with a patterned material that substantially resembles the environment in which the scent dispenser and scent attachment are deployed. In addition, the method can also include positioning a reflector responsive to light on the scent dispenser attachment to thereby permit the scent dispenser and scent dispenser attachment to be located in the dark with a generated beam of light.

The present invention further provides a method for marking a trail. The method specifically includes providing a plurality of self-fastening markers each of which contains a highly visible marking that can permit the user to readily locate by sight each of the plurality of markers.

BRIEF DESCRIPTION OF THE DRAWINGS

Some of the features, advantages, and benefits of the present invention having been stated, others will become apparent as the description proceeds when taken in conjunction with the accompanying drawings in which:

FIG. 1 is a perspective view of a combination scent dispenser and trail marking apparatus according to the present invention;

FIG. 2 is a perspective view of a combination scent dispenser and trail marking apparatus according to the present invention;

FIG. 3 is a perspective view of a combination scent dispenser and trail marking apparatus according to the present invention;

FIG. 4 is a perspective view of a combination scent dispenser and trail marking apparatus according to the present invention;

FIG. 5 is a perspective view of a combination scent dispenser and trail marking apparatus according to the present invention;

FIG. 6A is a perspective view of a combination scent dispenser and trail marking apparatus according to the present invention;

FIG. 6B is a fragmentary perspective view of the body of a combination scent dispenser and trail marking attachment according to the present invention;

FIG. 6C is a perspective view of a combination scent dispenser and trail marking apparatus according to the present invention;

FIG. 8 is a perspective view of a scent dispensing apparatus according to the present invention;

FIG. 9 is a perspective view of a scent dispensing apparatus according to the present invention;

FIG. 10 is a perspective view of a scent dispensing apparatus according to the present invention;

FIG. 11 is a perspective view of a scent dispensing apparatus according to the present invention; and FIG. 12 is a perspective view of a scent dispensing apparatus according to the present invention;

DETAILED DESCRIPTION OF THE PREFERRED EMBODIMENTS

Figure 7:
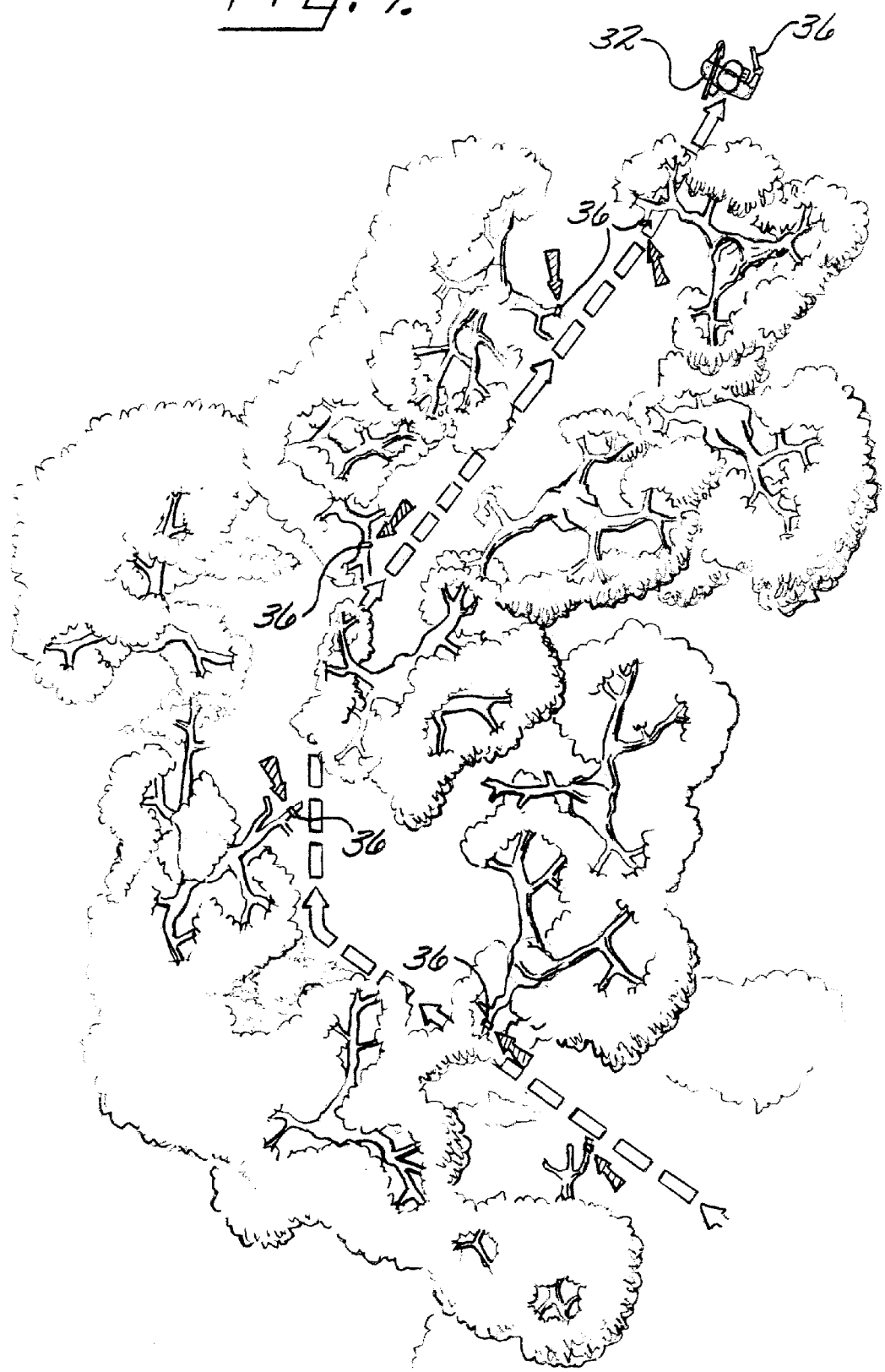
FIG. 7 is a top plan view of a scent dispensing and trail marking system being used along a trail by a hunter according to the present invention.

The present invention will now be described more fully hereinafter with reference to the accompanying drawings which illustrate preferred embodiments of the invention. The invention, however, may be embodied in many different forms and should not be construed as limited to the embodiments set forth herein. Rather, these embodiments are provided so that this disclosure will be thorough and complete and fully convey the scope of the invention to those skilled in the art. Like numbers refer to like elements throughout. The prime notation, if used, indicates similar elements in alternative embodiments.

FIGS. 1–12 illustrate an apparatus 30 for use by a hunter 32 to readily attach to and detach from a selected environmental structure a scent dispenser 34 that can also be used to mark the hunter's trail as well as indicate the hunter's presence to other hunters in the vicinity. As shown in FIG. 1, the apparatus 30 can be used to readily attach a scent dispenser 34 to the limb of a tree or bush. Alternatively, as illustrated in FIG. 2, the apparatus 30 can be readily attached to the hunter's person, such as also permits the hunter 32 to readily attach the scent dispenser 34 to the hunter's own person such as around the hunter's wrist, as well as, for example, around the hunter's ankle or arm. Just as readily, the apparatus 30 can be attached to the hunter's equipment or apparel, such as, for example, the hunter's cap or the laces of the hunter's boot. (See FIGS. 3 and 4).

As will be well appreciated by those skilled in the art, the scent dispenser 34 can be formed efficiently using an absorbent material such as a fibrous strip or a portion of a sponge that will readily absorb a scented substance. Alternatively, as also will be readily understood by those skilled in the art, the scent dispenser 34 instead can be formed from a rigid, scented substance such as wax or plastic. As explained below, the apparatus 30 according to the present, invention can accommodate any of the varied types of scent dispensers commonly employed by hunters. The scent itself can be any type of agent for attracting a hunted animal, such as a deer lure, or alternatively, a scent blocker meant to mask the scent of the hunter 32 and the hunter's apparel and equipment.

As perhaps best illustrated in FIG. 5, the apparatus 30 is readily attached to a pre-selected object by striking the pre-selected object with a scent dispenser attachment 36 to which the scent dispenser 34 is connected. Thus, the scent dispenser attachment 36 is adapted to receive and hold thereto the scent dispenser 34 and to self-fasten onto a pre-selected object against which the scent dispenser attachment 36 is struck using a moderate amount of force. Preferably, the scent dispenser attachment 36 is a generally rectangular strip biased to take on and remain in a coiled alignment unless stretched out into a substantially elongate shape.

More specifically, as illustrated in FIGS. 6A–6C, the scent dispenser attachment 36 comprises a substantially elongate body 38, preferably formed of a semi-rigid material. The substantially elongate body 38 of the scent dispenser attachment 36 has a substantially convex first surface 40, the direction of curvature of the convex surface being substantially perpendicular to the direction of elongation of the substantially elongate body 38, and a substantially concave second surface 42, the second surface 42 being opposite the first surface 40 and the direction of curvature of the concave surface, again, being substantially perpendicular to the direction of elongation of the substantially elongate body 38. Because the substantially elongate body 38 is intentionally formed with a bias toward a coiled alignment, the body 38 naturally possesses potential energy when stretched to its fully elongated shape. The convex first surface 40 and the concave second surface 42, however, impart a curvature along and, preferably, substantially centered around the longitudinal axis of the body 38. Thus formed, the scent dispenser attachment 36, despite its bias toward a coiled alignment can be stretched into a substantially elongate alignment with the convex and concave surfaces of the elongate body 38 supplying resistance to the body's natural tendency to coil. That is, despite the body's potential energy when stretched longitudinally, the curvature supplied by the shape of the convex surface 40 and the concave surface 42 allow the body 38 to remain in equilibrium. (See FIG. 6A).

When struck against a pre-selected object, however, the body's tendency to coil is not impeded, as the force of the blow tends to flatten out the convex and concave surfaces 40, 42. (See FIG. 6B). To attach the apparatus 30, therefore, the user need only strike the scent dispenser attachment 36 against the pre-selected object with enough force to overcome the obstacle posed by the curvature around the longitudinal axis formed as a result of the convexity of the first surface 40 and concavity of the second surface 42. As the respective surfaces flatten out, the released potential energy is made available to drive the body 38 into a more stable equilibrium: a coiled alignment. (See FIG. 6C). Thus, when struck against the pre-selected object, the scent dispenser attachment 36 self-fastens by coiling substantially around the object against which it has struck. (See FIGS. 6B–6C).

Alternatively, the attachment can have an elongated body having a hollow portion that admits air and expels air by means, for example, of a squeeze bulb attached at an end of the elongated body. Air can be squeezed into the hollow portion so as to extend the otherwise coiled body. In the extended position, the device can be positioned adjacent a tree limb or similar object. Then, when the air is expelled (e.g., by release of pressure on the squeeze bulb described above), the body fastens to the limb or other object by returning to a coiled position.

The self-fastening capability of the scent dispenser attachment 36 provides the apparatus 30 considerable advantages. Among these are the ability of the user to be able to single handedly attach the scent dispenser 34 to a pre-selected object by simply tapping the scent dispenser 36 attachment against the pre-selected object with a modest amount of force. During a typical hunting excursion, the hunter 32 can move through a wooded area and, at selected points, stop and draw from his or her jacket a scent dispenser 34 connected to the scent dispenser attachment 36. (FIG. 7). Quietly, the hunter 32 can gently strike a tree limb or branch and thereby easily and quickly attach thereto the scent dispenser 34, the scent dispenser 34 having a deer lure or other animal-attracting agent. Thus, the hunter 32 can lay out a scent line leading directly to the hunter's stand. When the hunter 32 reaches his or her stand, another scent dispenser 34 can be attached using the scent dispenser attachment 36 to a rung on the ladder leading to the stand perched off the ground. The same apparatus 30 can just as readily be used with a scent blocker already described, in which case the scent dispenser 34 can be attached using the scent dispenser attachment 36 by threading it under the laces of the hunter's boot, tapping it against the hunter's ankle or wrist, or even wrapping it over the adjustment band of the hunter's cap. (FIGS. 1–4).

The body of the scent dispenser attachment 36 can be formed of any semi-rigid material such as a plastic or lightweight metal. Preferably, is formed of a lightweight metal such as carbonized steel. The body of the attachment 36, moreover, can serve dual functions, that of attaching to an object and also holding a scent, for example, by dousing a portion of the body in a scented substance such as a liquid scent. Alternatively, the scent dispenser 34 can be connected directly to the body, for example, by applying a strip having a first portion that is made of an absorbent material on which a scent is disposed and a second portion having an adhesive layer that adheres directly to the body formed of a light-weight metal or plastic.

Preferably, however, the apparatus 30 further includes a cover 44 that at least partially extends over the body of the scent dispenser attachment 36. More preferably, the cover 44 is formed of a material having a predetermined surface pattern. For example, the pattern can be a blend of colors that, depending on the season during which and the environment in which the apparatus 30 is to be used, will mimic the colors of the environment in which the hunter 32 is employing the apparatus 30. This permits the apparatus 30 to be easily camouflaged so as not to cause the hunter 32 to standout if he is wearing or carrying the apparatus 30. At the same time, the camouflage pattern masks the device so as not to ward off a hunter's prey if the apparatus 30 is positioned on a tree limb, ladder rung, or other object.

A typical outdoor or hunting environment, for example, is a wooded or heavily foliaged area. An appropriate pattern for the cover 44 in order to effectively camouflage the apparatus 30, then, would be a mix of hues of green and brown that correspond to the colors of the foliage. More specifically, theories of the psychology and physics of the human visual system (HVS) explain that the human eye can perceive three attributes of color: brightness, hue, and saturation. These three attributes correspond, respectively, to the luminance (or intensity) of the color, the predominant wavelength of reflected electromagnetic radiation associated with the color, and the purity of the color. Thus, in order to camouflage the apparatus 30, the cover 44, preferably, has a pre-selected patter comprising at least some green and some brown. In terms of the HVS, then, the color attributes of a first portion of the preselected pattern of the cover 44 include a hue of that portion of the visible spectrum of electromagnetic radiation of between about four hundred eighty five nanometers (490 nm) and about five hundred seventy five nanometers (570 nm). This provides green coloring to the cover 44, but it is also preferable to have mixed therewith some brown as well. Accordingly, the color attributes of a second portion of the preselected pattern of the cover 44 include a low to moderate saturation and a hue of that portion of the visible spectrum of electromagnetic radiation of between about five hundred seventy nanometers (570 nm) and seven hundred fifty nanometers (750 nm).

Other color patterns, of course, could also be employed for different environments. For example, in a desert environment, the mix of colors of the cover 44 can be more predominantly brown or a mixed pattern, portions of which having color attributes of low to moderate saturation and a hue from that portion of the visible spectrum of electromagnetic radiation of a between about five hundred seventy nanometers (570 nm) and seven hundred fifty nanometers (750 nm) along with some beige or tan hues. So too, for hunting in a winter environment, the pattern of the color would be exclusively or predominately white; that is, of a chromatic color of a surface reflecting electromagnetic radiation of each wavelength in the visible spectrum.

In conjunction with the camouflage pattern, the cover 44 preferably also includes as well at least one limited-size marker or indicator such as a highly visible orange spot 43. (See FIG. 8). This mark or indicator can serve two important purposes. First, it can alert another hunter 32 in the area to the presence of the hunter 32 using the apparatus 30. Likewise, it can mark-off for the hunter 32, the perimeter of his or her field of fire. Relatedly, the pattern can be one chosen so as to convey other information, such as range, so that the hunter 32 can gauge the range of fire from his or her stand to a selected position within the field of fire. Thus, the cover 44, depending on the selected pattern of the material used in forming it, can perform a variety of functions for the hunter 32. In the same vein, the cover 44 also can include a light reflective portion 45 so that the apparatus 30 can be located in the dark using light generated, for example, by a flashlight. (See FIG. 9).

In a first embodiment of the apparatus 30, the scent dispenser 34 connects directly to the cover 44. Preferably, scent dispenser 34 is an absorbent portion fixedly connected to or integrally formed as part of the cover 44 and to which a liquid scent can be applied. (See FIGS. 1–6A). Alternatively, however, a scent dispenser can be removably connected to the attachment 36. For example, the cover 44 can include a connective surface portion. The scent dispenser, then, can be formed of a material that readily intertwines with the connective surface portion. An example of this would be if the materials were of a hook-and-loop type such as sold under the Velcro name and well-understood by those skilled in the art.

In a second embodiment of the apparatus 130 as shown in FIG. 10, the cover 144 includes a pouch 148 within which may be held, for example, a scented wax or other solid or semi-solid scent dispenser 134 having a scent that is released into the surroundings as the scent dispenser is held within the pouch 148. The pouch 148 can be integrally formed with the remainder of the cover 144 that substantially surrounds the body 138 of the scent dispenser attachment, or alternatively, it can detachably be connected by strips of the complementary materials (e.g., hook-and-loop fastening materials) already described. In yet a third embodiment of the apparatus 230 as shown in FIG. 11, the cover could include a series of small pockets or loops 248 for retaining several capsules or other scent dispensers 234 in the fashion of a bandolier. In still a fourth embodiment of the apparatus 330 as shown in FIG. 12, the scent dispenser 334 can be integrally formed with the cover 344 substantially covering the body of the scent dispenser attachment 336. In this embodiment, the scent dispenser comprises an absorbent material that adheres (e.g., using hook-and-loop fastening) to a portion formed as part of the cover (e.g., also being a type of hook-and-loop material) as well as being adapted to absorb a preselected scented substance.

The cover 44 preferably also includes a signal responsive portion 45. The hunter 32 or another person in the vicinity can thus detect the location of the apparatus 30 by sending out a signal, such as a beam of light generated by a flashlight, to which the apparatus responds (e.g., by reflecting the light) so that the locations of the apparatus 30 and the hunter 32, if the hunter is near the apparatus 30, are made known. The signal responsive portion 45 can be a reflector and, preferably, is a reflective strip positioned along a border of the body of the attachment 36. (See FIG. 9). The reflector or reflective strip 36 is responsive to a beam of light such as that generated by a flashlight. This permits the hunter to locate the apparatus in the dark using the beam of a flashlight. Likewise, another hunter in the area can be warned of the hunter's presence in the vicinity if the apparatus 30 is attached to the person or an article of apparel of the hunter. Similarly, given the increasing use of dirt bikes by hunters, the apparatus 30 also could be attached to a part of a bike at night so that a hunter riding the bike could be seen in the headlights of a driver driving a vehicle in the vicinity of the hunter. So too, the same use could be made of the apparatus 30 by a jogger or bicyclist traveling along a road at night.

The present invention further provides a system for dispensing a scent, providing a scent blocker, and marking a trail. The system, according to the present invention, permits a hunter to carry a plurality of scent dispensers 34 as he or she moves through an environment during a hunting excursion. As noted above, the hunter is able to draw one of the plurality of scent dispensers and, at a series of selected points along a trail, readily attach the scent dispenser to a pre-selected object (e.g. tree limb, ladder rung, fence) so as to provide a prolonged source of scent conveyance with the scent dispenser 34 attached via the scent dispenser attachment 36 to the pre-selected object. (See FIG. 7). At the same time, the covers 44 substantially covering the bodies of the distributed scent attachments to which each of the scent dispensers is attached can serve various other functions, including marking the hunter's trail, marking the perimeter of the field of fire, and providing fire range gauges, as also noted above.

Furthermore, according to the system provided by the present invention, the hunter 32 is later able to move back along the trail finding his or her way by reference to the markings on the cover substantially covering the scent dispensing attachment. By looking for the bright mark 43 (e.g., orange spot) in daylight or the seeing the light reflected by the light reflector 45 in the dark, the hunter is able not only to find his or her original trail but also to located and retrieve each of the combination scent dispenser-markers so that the scent dispenser can be replenished and the system re-used during the hunter's next hunting excursion.

FIGS. 1 through 10 also illustrate the various method aspects of the present invention. The present invention provides a method for use by a hunter in dispensing a scent. Specifically, the method includes providing at least one scent dispenser 34 along with at least one scent dispenser attachment 36. According to the method of the present invention, the scent dispenser attachment is especially adapted to receive and hold a scent dispenser 34. Moreover, the at least one scent dispenser attachment 36 is capable of self-fastening to a pre-selected structure and a person and apparel of the person whenever a method user strikes the at least one scent dispenser attachment against an object.

The method, moreover, includes camouflaging the at least one scent dispenser 34 and scent dispenser attachment 36 by at least partially covering each with a patterned material wherein the pattern substantially resembles the environment in which the scent dispenser and scent attachment are deployed to thereby substantially camouflage both. In addition, the method also includes positioning a reflector 45 responsive to light on the scent dispenser attachment 36 to thereby permit the scent dispenser 34 and scent dispenser attachment 36 to be located in the dark with a generated beam of light.

The present invention further provides a method for marking a trail. The method specifically includes providing a plurality of self-fastening markers 30 each of which contains a highly visible marking 43 that can permit the method user to readily locate by sight each of the plurality of markers 30.

In the drawings and specification, there have been disclosed a typical preferred embodiment of the invention, and although specific terms are employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification and as defined in the appended claims.

What is claimed is:

1. A combination scent dispensing and trail marking apparatus readily attachable to and detachable from a pre-selected object for use by a hunter in dispensing a scented lure or scent blocker, marking the hunter's trail, and indicating to other hunters the hunter's presence, the apparatus comprising:
   a scent dispenser; and
   a self-fastening attachment positioned to receive and hold connected thereto the scent dispenser and to attach the scent dispenser to a preselected object, the self-fastening attachment comprising:
      a substantially elongate body formed of a semi-rigid material and having a substantially convex first surface wherein the direction of curvature of the convex surface is substantially perpendicular to the direction of elongation of the substantially elongate body and a substantially concave second surface opposite the first surface wherein the direction of curvature of the concave surface is substantially perpendicular to the direction of elongation of the substantially elongate body, and
      a cover extending at least partially around the substantially elongate body, being formed of a material having a preselected pattern to thereby correspond to the environment within which the apparatus is used such that the apparatus is substantially camouflaged by its surroundings and a light-reflective portion responsive to a beam of light such that the apparatus can be seen in the dark with a generated beam of light.

2. An apparatus as defined in claim 1, wherein the cover further comprises a fastener to which the scent dispenser can removably attach.

3. An apparatus as defined in claim 2, wherein the fastener and a portion of the scent dispenser are each composed of materials that readily intertwine to thereby detachably connect the scent dispenser to the cover of the attachment.

4. An apparatus as defined in claim 1, further comprising a holder connected to the cover and adapted to receive and contain substantially therein the scent dispenser.

5. An apparatus as defined in claim 1, wherein the scent dispenser comprises an absorbent material connected to the cover and adapted to absorb a preselected scented fluid.

6. An apparatus as defined in claim 1, wherein the color attributes of a first portion of the preselected pattern of the cover include a hue of that portion of the visible spectrum of electromagnetic radiation of between about four hundred eighty five nanometers (490 nm) and about five hundred seventy five nanometers (570 nm), and wherein the color attributes of a second portion of the preselected pattern of the cover include a low to moderate saturation and a hue of that portion of the visible spectrum of electromagnetic radiation of a between about five hundred seventy nanometers (570 nm) and seven hundred fifty nanometers (750 nm).

7. An apparatus as defined in claim 1, wherein the cover further comprises an indicator portion having color attributes that include a moderate to high saturation and a hue of that portion of the visible spectrum of electromagnetic radiation of at least about five hundred ninety nanometers (590 nm) to thereby make the portion more readily visible in daylight.

8. An apparatus as defined in claim 1, wherein the cover defines one of a plurality of covers, each of the plurality of covers being adapted to removably extend substantially around the body of the attachment and formed of a material having a pre-determined pattern that corresponds to a specific environment in which the apparatus is to be deployed.

9. An apparatus as defined in claim 1, wherein the thickness of the substantially elongate body of the self-fastening attachment as measured between the substantially convex first surface and the substantially concave second surface is less than about one-eighth of an inch (⅛").

10. An apparatus as defined in claim 9, wherein the length of the substantially elongate body of the self-fastening attachment as measured along the centered axis of the body extending in the direction of elongation is at least about five inches (5").

11. An apparatus as defined in claim 10, wherein the length of the substantially elongate body of the self-fastening attachment as measured along the centered axis of the body extending in the direction of elongation is no more than about inches twenty four inches (24").

12. An apparatus as defined in claim 11, wherein the substantially elongate body is formed of a lightweight metal.

13. A scent dispensing apparatus for use by a hunter, the apparatus comprising:
   a self-fastening attachment having a substantially elongate body formed of a semi-rigid material and having a substantially convex first surface wherein the direction of curvature of the convex surface is substantially perpendicular to the direction of elongation of the substantially elongate body and a substantially concave second surface opposite the first surface wherein the direction of curvature of the concave surface is substantially perpendicular to the direction of elongation of the substantially elongate body; and
   a cover extending at least partially around the self-fastening attachment, the cover adapted to receive a scent applied to the cover.

14. An apparatus as defined in claim 13, wherein the thickness of the substantially elongate body of the self-fastening attachment as measured between the substantially convex first surface and the substantially concave second surface is less than one-eighth of an inch (⅛").

15. An apparatus as defined in claim 13, wherein the length of the substantially elongate body of the self-fastening attachment as measured along the centered axis of the body extending in the direction of elongation is at least about five inches (5").

16. An apparatus as defined in claim 13, wherein the length of the substantially elongate body of the self-fastening attachment as measured along the centered axis of the body extending in the direction of elongation is no more than about inches twenty four inches (24").

17. An apparatus as defined in claim 13, wherein the substantially elongate body is formed of a lightweight metal.

18. A scent dispensing apparatus for use by a hunter to readily attach to and detach from a pre-selected environmental structure, the person, or apparel of the hunter a scent dispenser to conveniently dispense a scent to lure a hunted animal or mask odors associated with the hunter, or apparel, or equipment of the hunter, the apparatus comprising:
   a scent dispenser; and
   a self-fastening attachment positioned to receive and hold connected thereto the scent dispenser to thereby attach the scent dispenser to a preselected object, the self-fastening attachment comprising a substantially elongate body formed of a semi-rigid material and having a substantially convex first surface wherein the direction of curvature of the convex surface is substantially perpendicular to the direction of elongation of the substantially elongate body and a substantially concave second surface opposite the first surface wherein the direction of curvature of the concave surface is substantially perpendicular to the direction of elongation of the substantially elongate body.

19. An apparatus as defined in claim 18, wherein the thickness of substantially elongate body of the self-fastening attachment as measured between the substantially convex first surface and the substantially concave second surface is less than one-eighth of an inch (⅛").

20. An apparatus as defined in claim 19, wherein the length of the substantially elongate body of the self-fastening attachment as measured along the centered axis of the body extending in the direction of elongation is at least about five inches (5").

21. An apparatus as defined in claim 20, wherein the length of the substantially elongate body of the self-fastening attachment as measured along the centered axis of the body extending in the direction of elongation is no more than about inches twenty four inches (24").

22. An apparatus as defined in claim 21, wherein the substantially elongate body is formed of a lightweight metal.

23. A self-fastening scent dispenser for use by a hunter to readily attach to and detach from a pre-selected object, the dispenser comprising:
   a substantially elongate body portion formed of a semi-rigid material and having a substantially convex first surface wherein the direction of curvature of the convex surface is substantially perpendicular to the direction of elongation of the substantially elongate body and a substantially concave second surface opposite the first surface wherein the direction of curvature of the concave surface is substantially perpendicular to the direction of elongation of the substantially elongate body, the body adapted to receive a scent applied to the body;
   wherein a pattern is formed on at least a portion of the surface of the body, the pattern preselected to thereby correspond to the environment within which the apparatus is used such that the apparatus is substantially camouflaged; and
   wherein the dispenser is adapted to receive a scent applied thereto.

24. A dispenser as defined in claim 23, wherein the thickness of substantially elongate body as measured between the substantially convex first surface and the substantially concave second surface is less than one-eighth of an inch (⅛").

25. A dispenser as defined in claim 23, wherein the length of the substantially elongate body as measured along the centered axis of the body extending in the direction of elongation is at least about five inches (5").

26. A dispenser as defined in claim 23, wherein the length of the substantially elongate body as measured along the centered axis of the body extending in the direction of elongation is no more than about inches twenty four inches (24").

27. A dispenser as defined in claim 23, wherein the color attributes of a first portion of the preselected pattern positioned on the substantially elongate body include a hue of that portion of the visible spectrum of electromagnetic radiation of between about four hundred eighty five nanometers (490 nm) and about five hundred seventy five nanometers (570 nm), and wherein the color attributes of a second portion of the preselected pattern of the cover include a low to moderate saturation and a hue of that portion of the visible spectrum of electromagnetic radiation of a between about five hundred seventy nanometers (570 nm) and seven hundred fifty nanometers (750 nm).

28. A dispenser as defined in claim 23, further comprising a distinctive marking positioned on the substantially elongate body, wherein the color attributes of the distinctive marking include a moderate to high saturation and a hue of that portion of the visible spectrum of electromagnetic radiation of at least about five hundred ninety nanometers (590 nm).

29. A dispenser as defined in claim 23, wherein the dispenser further comprises a reflector positioned on the substantially elongate body, the reflector being responsive to light to enable an observer to detect the location of the apparatus using a generated beam of light.

30. A self-fastening scent dispenser for use by a hunter to readily attach to and detach from a pre-selected object, the dispenser comprising:
- a substantially elongate body portion formed of a semi-rigid material and having a substantially convex first surface wherein the direction of curvature of the convex surface is substantially perpendicular to the direction of elongation of the substantially elongate body and a substantially concave second surface opposite the first surface wherein the direction of curvature of the concave surface is substantially perpendicular to the direction of elongation of the substantially elongate body, the body adapted to receive a scent applied to the body, wherein the dispenser is adapted to receive a scent applied thereto.

31. A dispenser as defined in claim 30, wherein the thickness of substantially elongate body as measured between the substantially convex first surface and the substantially concave second surface is less than one-eighth of an inch (⅛").

32. A dispenser as defined in claim 30, wherein the length of the substantially elongate body as measured along the centered axis of the body extending in the direction of elongation is at least about five inches (5").

33. A dispenser as defined in claim 30, wherein the length of the substantially elongate body as measured along the centered axis of the body extending in the direction of elongation is no more than about inches twenty four inches (24").

34. A combination trail marking and presence indicating apparatus for marking a user's trail within an outdoor environment and warning of the user's presence to other persons in the vicinity of the user, the apparatus comprising:
- a self-fastening attachment having a substantially elongate body formed of a semi-rigid material and having a substantially convex first surface wherein the direction of curvature of the convex surface is substantially perpendicular to the direction of elongation of the substantially elongate body and a substantially concave second surface opposite the first surface wherein the direction of curvature of the concave surface is substantially perpendicular to the direction of elongation of the substantially elongate body; and
- a cover extending at least partially around the self-fastening attachment, the cover being formed of a material having a preselected pattern to thereby correspond to the environment within which the apparatus is used such that the apparatus is substantially camouflaged and having at least one distinctive marking to draw the attention of an observer observing the environment.

35. An apparatus as defined in claim 34, wherein the thickness of substantially elongate body of the self-fastening attachment as measured between the substantially convex first surface and the substantially concave second surface is less than one-eighth of an inch (⅛").

36. An apparatus as defined in claim 34, wherein the length of the substantially elongate body of the self-fastening attachment as measured along the centered axis of the body extending in the direction of elongation is at least about five inches (5").

37. An apparatus as defined in claim 34, wherein the length of the substantially elongate body of the self-fastening attachment as measured along the centered axis of the body extending in the direction of elongation is no more than about twenty four inches (24").

38. An apparatus as defined in claim 34, wherein the color attributes of a first portion of the preselected pattern of the cover include a hue of that portion of the visible spectrum of electromagnetic radiation of between about four hundred eighty five nanometers (490 nm) and about five hundred seventy five nanometers (570 nm), and wherein the color attributes of a second portion of the preselected pattern of the cover include a low to moderate saturation and a hue of that portion of the visible spectrum of electromagnetic radiation of a between about five hundred seventy nanometers (570 nm) and seven hundred fifty nanometers (750 nm).

39. An apparatus as defined in claim 34, wherein the color attributes of the distinctive marking include a moderate to high saturation and a hue of that portion of the visible spectrum of electromagnetic radiation of at least about five hundred ninety nanometers (590 nm).

40. An apparatus as defined in claim 34, wherein the cover further comprises a reflective portion responsive to light to enable an observer to detect the location of the apparatus using a generated beam of light.

41. An apparatus as defined in claim 34, wherein the cover defines one of a plurality of covers, each of the plurality of covers is adapted to removably extend substantially around the body of the attachment and is formed of a material having a pre-determined pattern that corresponds to a specific environment in which the apparatus is to be deployed.

42. A self-fastening trail marking and presence indicating apparatus for use in an outdoor environment, the apparatus comprising:
- a substantially elongate body formed of a semi-rigid material and having a substantially convex first surface wherein the direction of curvature of the convex surface is substantially perpendicular to the direction of elongation of the substantially elongate body and a substantially concave second surface opposite the first surface wherein the direction of curvature of the concave surface is substantially perpendicular to the direction of elongation of the substantially elongate body, the body adapted to receive a scent applied to the body; and
- a surface portion of the substantially elongate body being conspicuously visible to a human eye to thereby readily attract the attention of an observer within the vicinity of the marker.

43. An apparatus as defined in claim 42, wherein the color attributes of at least a first portion of the surface portion include a hue of that portion of the visible portion of the electromagnetic spectrum of at least about five hundred fifty five nanometers (555 nm).

44. An apparatus as defined in claim 42, wherein at least a portion of the surface portion is light-reflective to thereby permit each of the plurality of markers to be visible to a human eye in a dark environment when a light is shone on the surface portion.

45. A system for dispensing a scent to be used by a hunter, the system comprising:
- a plurality of scent dispensers; and
- a plurality of attachments, each one of the plurality of attachments uniquely corresponding to and positioned to receive and hold thereto one of the plurality of scent dispensers and comprising a substantially elongate body formed of a semi-rigid material and having a substantially convex first surface wherein the direction of curvature of the convex surface is substantially perpendicular to the direction of elongation of the substantially elongate body and a substantially concave second surface opposite the first surface wherein the direction of curvature of the concave surface is substantially perpendicular to the direction of elongation of the substantially elongate body.

46. A system as defined in claim 45, wherein each of the plurality of scent dispenser attachments further comprises a cover extending at least partially around the substantially elongate body.

47. A system as defined in claim 46, wherein each cover comprises a predetermined pattern of colors corresponding to those predominant within the environment in which the system is used to thereby substantially camouflage each of the plurality of scent dispensers and corresponding attachments.

48. A system as defined in claim 47, wherein each cover further includes a light-reflective portion responsive to a beam of light such that the scent dispenser and scent dispenser attachment can be located in the dark with a generated beam of light.

49. A system as defined in claim 48, wherein each cover further includes an indicator portion that can be readily seen in the daylight.

50. A trail marking system for use during outdoor activities to readily mark a trail, the system comprising a plurality of markers to readily attach to and detach from a preselected structure, each marker comprising substantially elongate body formed of a semi-rigid material and having a substantially convex first surface wherein the direction of curvature of the convex surface is substantially perpendicular to the direction of elongation of the substantially elongate body, a substantially concave second surface opposite the first surface wherein the direction of curvature of the concave surface is substantially perpendicular to the direction of elongation of the substantially elongate body, and a surface portion conspicuously visible to a human eye to thereby readily attract the attention of an observer within the vicinity of the marker.

51. A system as defined in claim 50, wherein a color attribut of at least a first portion of the surface portion is a hue of that portion of the visible portion of the electromagnetic spectrum of at least about five hundred fifty five nanometers (555 nm).

52. A system as defined in claim 51, wherein at least a portion of the surface portion is light-reflective to thereby permit each of the plurality of markers to be visible to a human eye in a dark environment when a light is shone on the surface portion.

* * * * *